US00PP34079P2

(12) United States Plant Patent
Ammerlaan

(10) Patent No.: US PP34,079 P2
(45) Date of Patent: Mar. 29, 2022

(54) ***GASTERALOE* PLANT NAMED 'OVROCKS08'**

(50) Latin Name: *xGasterloe beguinii*
Varietal Denomination: OVROCKS08

(71) Applicant: Ovata B.V., Bleiswijk (NL)

(72) Inventor: Johannes Hendrikus Adrianus Ammerlaan, Bleiswijk (NL)

(73) Assignee: Ovata B. V., Bleiswijk (NL)

( * ) Notice: Subject to any disclaimer, the term of this patent is extended or adjusted under 35 U.S.C. 154(b) by 0 days.

(21) Appl. No.: 17/300,811

(22) Filed: Nov. 12, 2021

(30) Foreign Application Priority Data

Nov. 13, 2020 (QZ) ..... PBR 2020/2874

(51) Int. Cl.
*A01H 6/00* (2018.01)
*A01H 5/12* (2018.01)

(52) U.S. Cl.
USPC ..... Plt./373

(58) Field of Classification Search
USPC ..... Plt./373
CPC ..... A01H 6/00
See application file for complete search history.

*Primary Examiner* — Keith O. Robinson
(74) *Attorney, Agent, or Firm* — Samuel R. McCoy, Jr.

(57) ABSTRACT

A new and distinct x *Gasteraloe* plant named 'OVROCKS08' which is characterized by dark green foliage that is moderately to densely covered with very light greyed-green protuberances randomly arranged on the leaf surface, protuberances along the distal centerline of the abaxial foliar surface that are arranged in a distinct line and modified into spines like those of the foliar margins, and finely dentate margins with very light greyed-green teeth. The new variety has shown to be uniform and stable in the resulting generations from asexual propagation.

4 Drawing Sheets

Latin name of the genus and species: The Latin name of the genus and species of the novel variety disclosed herein is x*Gasteraloe beguinii.*

Variety denomination: The inventive variety of x*Gasteraloe* disclosed herein has been given the variety denomination 'OVROCKS08'.

CROSS REFERENCE TO RELATED APPLICATIONS

This application claims priority to the Community Plant Variety Rights application number 2020/2874, filed on Nov. 13, 2020, which is herein incorporated by reference.

BACKGROUND OF THE INVENTION

Parentage: 'OVROCKS08' originated as a naturally occurring, whole-plant mutation of an unnamed x*Gasteraloe beguinii* plant (not patented). The inventor of 'OVROCKS08' is a commercial ornamental plant producer and regularly discovers mutations of x*Gasteraloe* at his greenhouse operation in Bleiswijk, The Netherlands. For said mutations which seem to exhibit commercial potential, cuttings are taken to produce trial plants which are subsequently grown for evaluation.

The variety now called 'OVROCKS08' was initially discovered in the summer of 2016 as a whole-plant mutation of an unnamed x*Gasteraloe* plant which exhibited dark green foliage, lighter green near the base, with uniquely arranged foliar protuberances and dentate foliar margins. At the time of discovery, cuttings were taken and the resulting plants were evaluated at the inventor's greenhouse. After further evaluation it was determined that the candidate plant's unique foliage characteristics would prove favorable for commercial marketability. The new plant was given the denomination 'OVROCKS08'.

Asexual Reproduction: The variety now called 'OVROCKS08' was first asexually propagated by stem cuttings in the summer of 2016 at a greenhouse in Bleiswijk, The Netherlands and has since been vegetatively propagated through four additional generations. Through subsequent generations, the unique features of this cultivar are stable and reproduced true to type.

SUMMARY OF THE INVENTION

The cultivar 'OVROCKS08' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'OVROCKS08'. These characteristics in combination distinguish 'OVROCKS08' as a new and distinct x*Gasteraloe* cultivar:

1. 'OVROCKS08' exhibits lanceolate foliage, with a long mucronate tip, growing in a compact basal rosette with secondary rosettes eventually developing at the base of the primary rosette; and
2. 'OVROCKS08' exhibits relatively dark green foliage that is moderately to densely covered with very light greyed-green protuberances that are randomly arranged on the leaf surface; and
3. 'OVROCKS08' exhibits a subset of protuberances along the distal centerline of the abaxial foliar surface, arranged in a distinct line, that are modified into spines; and 4. 'OVROCKS08' exhibits finely dentate margins with very light greyed-green teeth.

BOTANICAL DESCRIPTION OF THE PLANT

Figure 1:
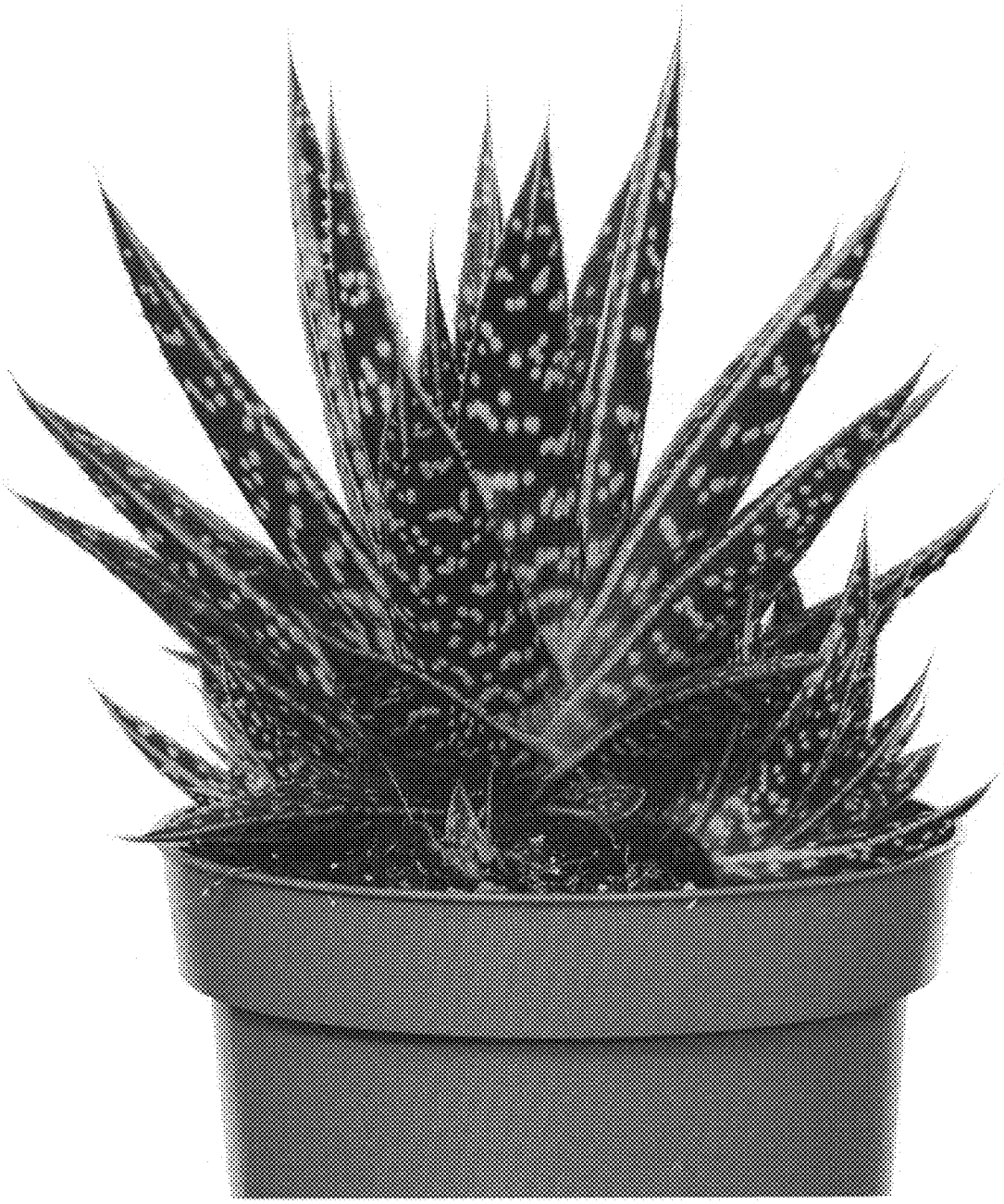
FIG. 1 illustrates, as nearly true as it is reasonably possible to make the same in color photographs of this type, an exemplary plant of 'OVROCKS08' grown in a commercial greenhouse in Bleiswijk, the Netherlands. This plant is approximately 1 year old, shown planted in a 12 cm container.
Figure 2:
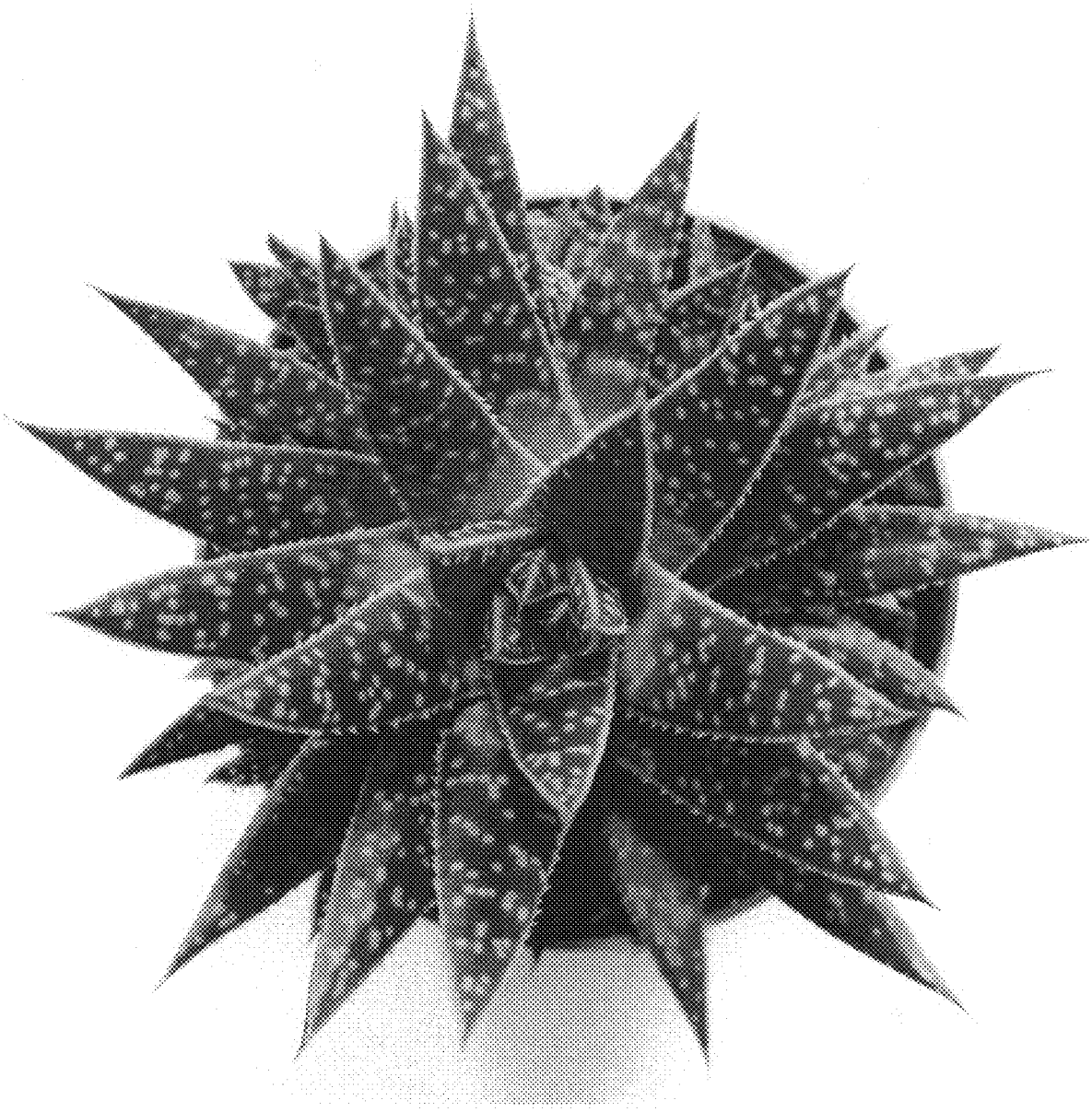
FIG. 2 illustrates, as nearly true as it is reasonably possible to make the same in color photographs of this type, the typical foliage arrangement of 'OVROCKS08'.
Figure 3:
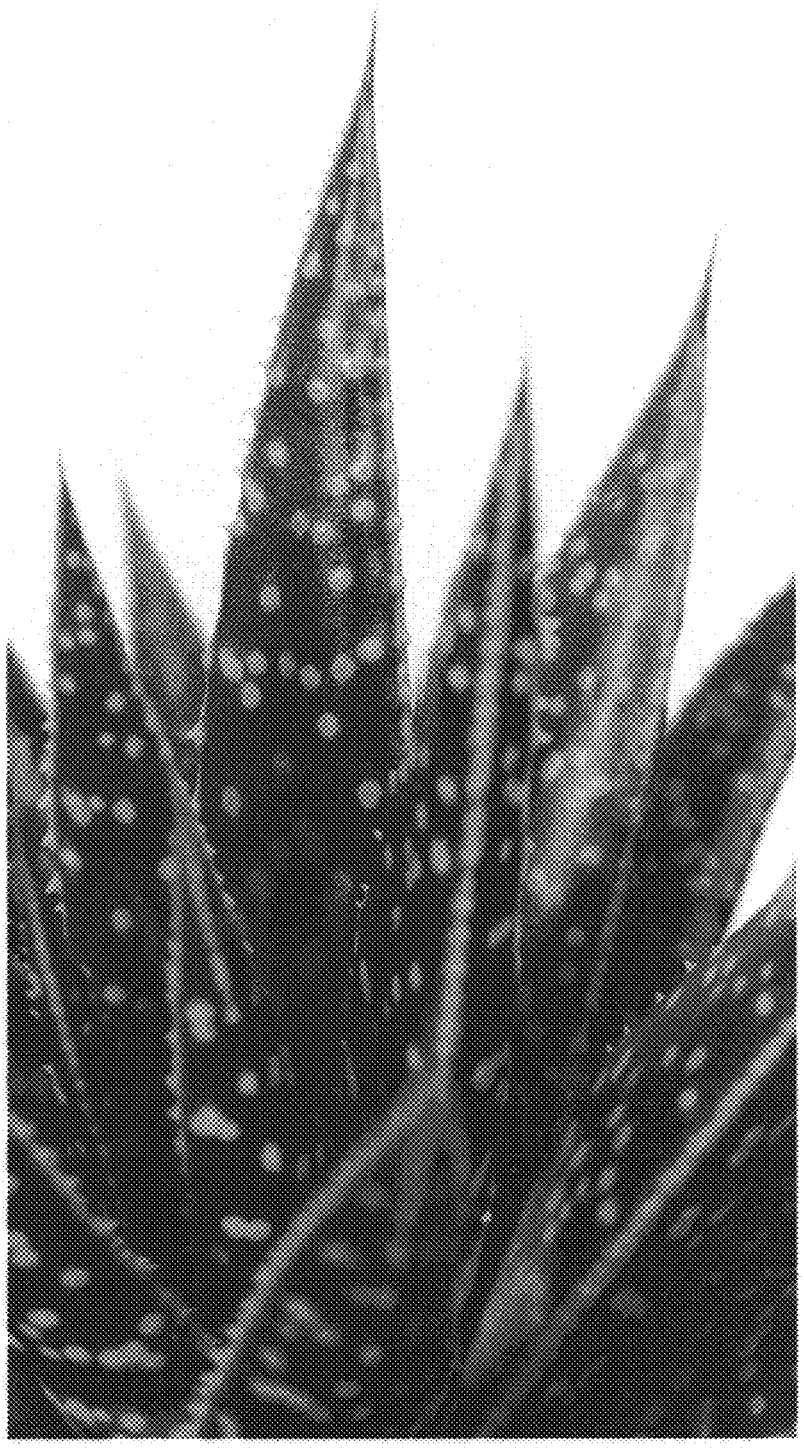
FIG. 3 illustrates, as nearly true as it is reasonably possible to make the same in color photographs of this type, the adaxial surface of the mature foliage 'OVROCKS08'.
Figure 4:
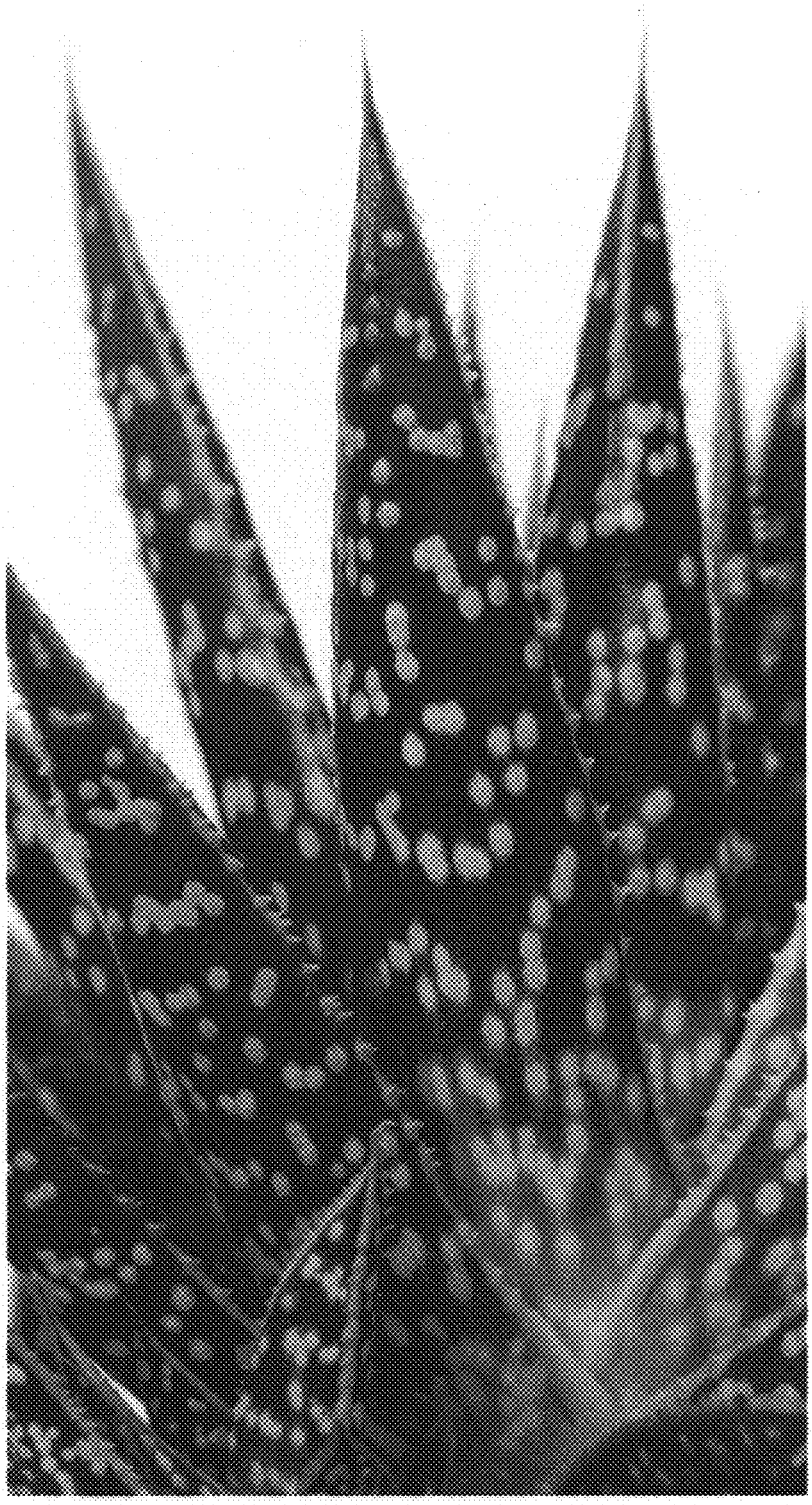
FIG. 4 illustrates, as nearly true as it is reasonably possible to make the same in color photographs of this type, the abaxial surface of the mature foliage 'OVROCKS08'.

The following observations and measurements made in November of 2020 describe averages from a sample set of six specimens of 1 year old 'OVROCKS08' plants grown in 12 cm nursery containers at commercial greenhouse in Bleiswijk, the Netherlands. Plants were produced using conventional greenhouse production protocols for x*Gasteraloe* which consisted of minimal overhead irrigation and fertilizer applications. No pest or disease control measures were utilized in production. Plants were grown under shade (approximately 10,000 lux) and no photoperiodic treatments or artificial light was given to the plants.

Those skilled in the art will appreciate that certain characteristics will vary with older or, conversely, with younger plants. 'OVROCKS08' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'OVROCKS08' and a comparison with the parent and closest known comparator is provided below.

Plant description:

*Growth habit*.—Succulent perennial with foliage growing in a compact basal rosette; as plants age, secondary rosettes eventually develop at the base of the primary rosette.

*Plant form*.—Globular.

*Height from soil level to top of foliar plane*.—12.8 cm.

*Plant spread*.—Average of 15.5 cm.

*Growth rate*.—Slow to moderate rate of growth.

*Plant vigor*.—Moderately vigorous.

*Propagation*.—Type — Leaf cuttings. Time to initiate rooting — Approximately 5 weeks at an approximate temperature of 21 degrees Celsius. Crop time — Approximately 1 year to produce a marketable plant in a 9 cm container.

*Disease and pest resistance or susceptibility*.—Neither resistance nor susceptibility to typical x*Gasteraloe* pests and diseases has been observed.

*Environmental tolerances*.—Adapt to, at least, USDA Zones 10 to 12 and temperatures as high as 40 degrees Celsius; moderate tolerance to rain yet drought tolerant once established; high tolerance to wind.

Root system:

*General*.—Fine, well-branched fibrous roots.

Stems:

*Branching habit*.—No stems or branches; leaves arranged in a basal rosette.

Foliage:

*Arrangement*.—Spirally arranged in a basal rosette.

*Division*.—Simple.

*Attachment*.—Sessile.

*Quantity*.—Approximately 33 leaves per rosette.

*Shape*.—Lanceolate.

*Dimensions*.—9.0 cm long, 2.6 cm wide, and 1.2 cm thick.

*Aspect*.—Flat to very slightly concave.

*Attitude*.—Foliage is held upright at and near the center of the rosettes and becomes progressively more relaxed towards the outer whorls of foliage, at an average angle of 50 degrees from horizontal; lamina is very slightly curled downward with the distal portion at and near the apex being slightly curled upward.

*Apex*.—Apiculate with a long, soft mucronate tip.

*Base*.—Broad cuneate.

*Margin*.—Finely dentate; teeth have an average length of 0.75 cm and are colored greyed-green, nearest to RHS 191B. Margins are not undulated or lobed.

*Pubescence and texture of the adaxial surface*.—Glabrous, smooth, and moderately to densely covered with small, round protuberances that are randomly arranged on the leaf surface; protuberances are approximately 0.175 cm in diameter.

*Pubescence and texture of the abaxial surface*.—Glabrous, smooth, and moderately to densely covered with small, round protuberances that are randomly arranged on the leaf surface; protuberances are approximately 0.2 cm long and 0.15 cm wide. A small subset of protuberances along the distal centerline are arranged in a distinct line and are modified into spines. These spines are similar in size and color to the dentate teeth along the foliar margins.

*Luster of the adaxial surface*.—Moderately glossy.

*Luster of the abaxial surface*.—Moderately glossy.

*Color*.—Juvenile foliage, adaxial surface — Green, nearest to in between RHS NN137A and 137A, and fading to yellow-green towards the base, nearest to a mixture of RHS 145A and 146D. Protuberances are colored greyed-green, nearest to a mixture of RHS 193A and 193B. Juvenile foliage, abaxial surface — Green, nearest to a mixture of RHS NN137A and NN139A, and fading to yellow-green towards the base, nearest to RHS 145A. Protuberances are colored greyed-green, nearest to a mixture of RHS 193A and 193B. Mature foliage, adaxial surface — Nearest to in between green and yellow-green, RHS 139A and 147A yet slightly darker; fading to yellow-green towards the base, nearest to a mixture of RHS N148B and N148C. Protuberances are colored greyed-green, nearest to a mixture of RHS 191A and 191B. Mature foliage, abaxial surface — Nearest to in between green and yellow-green, RHS NN137A and 147A; fading to yellow-green towards the base, nearest to in between RHS 147D and 148D. Protuberances are colored greyed-green, nearest to RHS 191C.

*Venation*.—Pattern — No venation is visible. Color, adaxial surface — No venation is visible. Color, abaxial surface — No venation is visible.

*Petiole*.—No petiole; leaves are sessile.

Inflorescence: No flowering has been observed to date.

Comparisons With the Parent Plants

Plants of the new cultivar 'OVROCKS08' differ from the seed parent, an unnamed x*Gasteraloe* plant (not patented), in the following characteristics described in Table 1 below.

TABLE 1

| Characteristic | 'OVROCKS08' | The parent. |
|---|---|---|
| Foliage attitude. | More upright than the parent. | More relaxed than 'OVROCKS08'. |
| Foliage shape. | Narrower than the parent. | Broader than 'OVROCKS08'. |
| Foliage thickness. | Thinner than the parent. | Thicker than 'OVROCKS08'. |
| Foliar apex. | Mucronate tip is longer than that of the parent. | Mucronate tip is shorter than that of 'OVROCKS08'. |
| General coloration of the foliage. | In between green and yellow-green; generally appearing as lighter green by comparison to the parent. | In between green and greyed-green; generally appearing as darker green by comparison to 'OVROCKS08'. |

Comparison With the Closest Known Comparator

Plants of the new cultivar 'OVROCKS08' differ from the most similar variety known to the inventor, x*Gasteraloe* 'OVROCKS02' (U.S. Plant Pat. No. 30,136), in the following characteristics described in Table 2 below.

TABLE 2

| Characteristic | 'OVROCKS08' | 'OVROCKS02' |
|---|---|---|
| Growth habit. | Basal rosette with secondary rosettes eventually developing at the base of the primary rosette | Basal rosette that only occasionally develops secondary rosettes. |
| Foliage shape. | Lanceolate. | Narrow deltoid. |
| Foliage attitude. | More upright than 'OVROCKS02'. | More relaxed than 'OVROCKS08'. |
| General color. ation of the foliage. | In between green and dark yellow-green; generally appearing as darker green by comparison to 'OVROCKS02'. | In between green and yellow-green; generally appearing as lighter green by comparison to 'OVROCKS08'. |
| General coloration of foliar margins. | Colored the same as the balance of the lamina. | Leaves are margined light greyed-green. |
| Arrangement of the foliar protuberances. | Randomly arranged on the leaf surface. | Loosely arranged in axial rows across the leaf surface. |
| Prominence of dentate teeth along the foliar margins. | More prominent. | Less prominent. |

That which is claimed is:

1. A new and distinct variety of x*Gasteraloe* plant named 'OVROCKS08', substantially as described and illustrated herein.

* * * * *